July 31, 1973 J. R. CULBERT Plant Pat. 3,379
CHRYSANTHEMUM PLANT
Filed Sept. 30, 1971
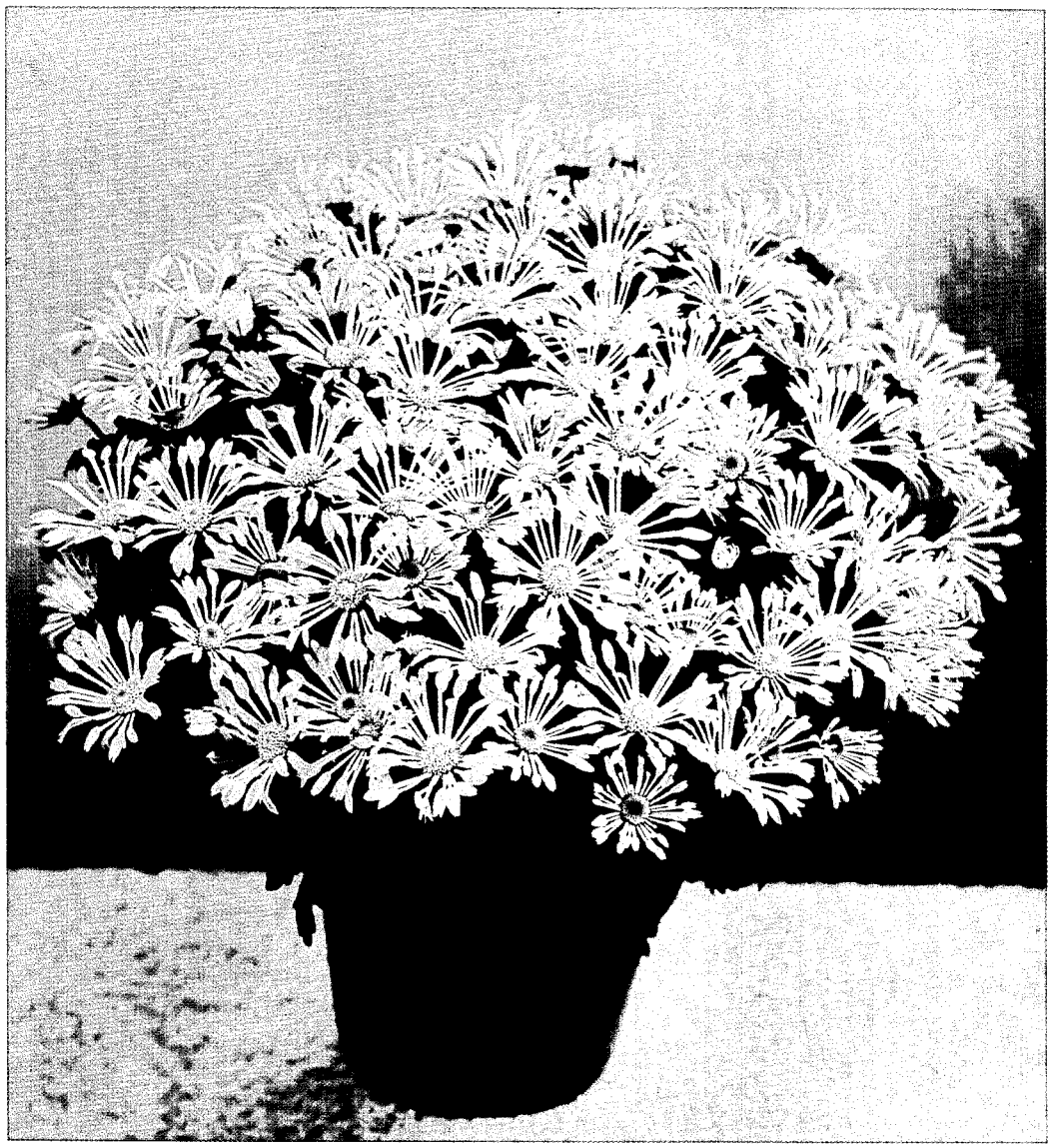

United States Patent Office

Plant Pat. 3,379
Patented July 31, 1973

3,379
CHRYSANTHEMUM PLANT

John Robert Culbert, Monticello, Ill., assignor to University of Illinois Foundation, Urbana, Ill.

Filed Sept. 30, 1971, Ser. No. 185,457
Int. Cl. A01h 5/00
U.S. Cl. Plt.—74 1 Claim The present invention relates to a new and distinct cultivar of chrysanthemum plant asexually reproduced by cuttings from a seedling selected from among the progeny of the cross of unpatented parent plants selected from among the stocks maintained by the Floriculture Department of the University of Illinois, Urbana, Ill. and identified for breeding purposes as Nos. 0–411 and 1–439.

Successive propagations of my new cultivar have retained the distinctive unique characteristics thereof, to wit:

(1) Pure white spoon tipped daisy flowers 1¾" to 2¼" in diameter;

(2) Plants that average 5 to 7 breaks per pinched plant;

(3) Prolific flowering habit in that well grown spray type six inch pots with five cuttings will produce 80 to 100 flowers;

(4) Efficient reproduction characteristics requiring only 9 to 10 weeks total crop time.

My new cultivar, when grown in the vicinity of Barberton, Ohio, has a response period of approximately 8–9 weeks, and the following detailed description is based on observations made of the new cultivar in a greenhouse in Barberton, Ohio. The response time, blooming period, color, and total vigor may vary significantly with varying environmental conditions such as temperature, day length, and light intensity.

The following chart outlines the variation in response experienced and the suggested long day treatment for the various seasons in Barberton, Ohio with carbon dioxide injected into the greenhouse when possible.

| Months: | Response pattern in the North |
|---|---|
| April–July | Early 8 |
| August and September | Mid 8 |
| October and November | Early 9 |
| December | Mid 8 |

Suggested flowering in the northern and western United States is from April through December; coastal California, January through December; Florida, November through December, and March through May.

The accompanying drawing shows the unique characteristics of my new cultivar, the color being as nearly true as possible with color illustrations of this type. Color references are made to the Munsell Color Book, 1963 edition.

Botanical classification: *Chrysanthemum morifolium.*

Bloom:

*Size.*—1¾".

*Fully expanded.*—2¼".

*Borne.*—Clusters on elongated pedicels.

*Stems.*—Strong.

*Form.*—Spooned tip daisy.

*Permanence.*—10–12 days.

*Color* (Munsell).—Center of flower—green, 5GY6/6, base of petals—yellow green, 2.5GY8/10, inside of petals—ivory, 10Y9/2 to pink 5R5/8, reverse of petals—ivory, 10Y9/1, tonality from a distance—white, discoloration—pink, 5R5/8.

Petals:

*Texture.*—Smooth.

*Appearance and form.*—Tubular flaring to spoon tip tapering to a blunt multinotched point.

*Arrangement.*—Composite, whorled on a single receptacle.

*Persistence.*—Resist shatter.

*Fragrance.*—Typical chrysanthemum.

Reproductive organs:

*Stamen, anthers.*—150–180.

*Pollen.*—Abundant.

*Arrangement.*—Clustered in center of flower, if present.

*Styles.*—Present both ray and disc florets.

*Length.*—Short.

*Ovaries.*—At the base of petal attached to receptacle.

Plant:

*Form.*—Herbaceous.

*Growth.*—Spreading.

*Height.*—11" to 13" when given 8 to 9 week medium to tall treatment during the various seasons of the year.

*Spread.*—8" when given 8 to 9 week medium to tall treatment during the various seasons of the year.

Foliage:

*Top side.*—Dark green, 7.5GY3/4.

*Size.*—6½" long. 3¾" wide.

*Quantity.*—Numerous.

*Shape.*—Spatulate lobed.

*Texture.*—Coarse.

*Ribs and veins.*—Prominent.

*Edge.*—Deeply indented.

*Serration.*—Deeply serrated.

*Under side.*—Light green, 7.5GY5/4.

*Stipules.*—Rudimentary.

What is claimed is:

1. A new and distinct cultivar of crysanthemum plant substantially as herein shown and described, characterized particularly as to novelty by pure spoon tipped daisy flowers 1¾" to 2¼" in diameter, plants that average 5 to 7 breaks per pinched plant, a prolific flowering habit in that well grown spray type six inch pots with 5 cuttings will produce 80 to 100 flowers, and efficient reproduction characteristics requiring only 9 to 10 weeks total crop time.

No references cited.

ROBERT E. BAGWILL, Primary Examiner